(12) United States Patent
Broneske et al.

(10) Patent No.: US 7,425,441 B2
(45) Date of Patent: Sep. 16, 2008

(54) BIOREACTOR FOR CULTURING MICROORGANISMS

(75) Inventors: Jürgen Broneske, OT Felgentreu (DE); Horst Franke, Mietgendorf (DE); Otto Pulz, OT Bergholz-Rehbrücke (DE); Heinz-Rüdiger Keitel, Obermelsungen (DE); Wolf-Dietrich Linke, Homberg/Efze (DE); Bernd-Ulrich Wilhelm, Petershagen (DE); Rainer Salzmann, Melsungen (DE); Wolfgang Kröger, Schauenburg (DE); Mirko Riese, Felsberg (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 673 days.

(21) Appl. No.: 11/103,148

(22) Filed: Apr. 11, 2005

(65) Prior Publication Data
US 2005/0255584 A1    Nov. 17, 2005

(30) Foreign Application Priority Data
Apr. 16, 2004 (DE) .................. 10 2004 019 234

(51) Int. Cl.
*C12M 1/42* (2006.01)
(52) U.S. Cl. .............. 435/292.1; 435/287.1; 435/295.2; 47/1.4
(58) Field of Classification Search .............. 435/293.1, 435/295.2, 257.1, 261, 420
See application file for complete search history.

(56) References Cited

U.S. PATENT DOCUMENTS

| | | | | |
|---|---|---|---|---|
| 3,957,585 A | * | 5/1976 | Malick | ................ 435/246 |
| 3,986,297 A | * | 10/1976 | Ichimura et al. | ......... 435/292.1 |
| 4,236,349 A | * | 12/1980 | Ramus | ................... 47/1.4 |
| 4,676,956 A | * | 6/1987 | Mori | ..................... 422/186 |
| 4,952,511 A | * | 8/1990 | Radmer | ............... 435/292.1 |
| 5,073,491 A | * | 12/1991 | Familletti | ............... 435/382 |
| 5,555,676 A | * | 9/1996 | Lund | ....................... 47/82 |
| 2005/0064577 A1 | * | 3/2005 | Berzin | .................... 435/266 |

FOREIGN PATENT DOCUMENTS

DE         19747994         * 1/1999

OTHER PUBLICATIONS

Christian Walter, Torsten Steinau, Norbert Gerbsh, Rainer Buchholz "Monoseptic cultivation of phototrophic microorganisms—development and scale-up of a photobioreactor system with thermal sterilization." Biomolecular Engineering 2003 v. 20 pp. 261-271. Elsevier.*

* cited by examiner

*Primary Examiner*—William H. Beisner
*Assistant Examiner*—Michael Hobbs
(74) *Attorney, Agent, or Firm*—Anthony J. Casella; Gerald E. Hespos

(57) ABSTRACT

A bioreactor for culturing microorganisms which has a reactor vessel, a plurality of gas-introduction tubes and a gas-introduction system for introducing gas into a culture medium in the gas-introduction tubes via injectors, wherein the gas-introduction tubes are connected by their respective lower end, in the vertical direction, to the reactor vessel and by their opposite upper end to the upper end of an upright vessel which is likewise connected by its lower end to the reactor vessel, and at the upper end of the upright vessel an expansion vessel is arranged.

22 Claims, 3 Drawing Sheets

BIOREACTOR FOR CULTURING MICROORGANISMS

BACKGROUND OF THE INVENTION

1. Field of the Invention

The invention relates to a bioreactor for culturing microorganisms which has a reactor vessel, a plurality of gas-introduction tubes and a gas-introduction system for introducing gas into a culture medium in the gas-introduction tubes via injectors.

2. Description of the Related Art

It is known to use photobioreactors for culturing phototropic microorganisms, in particular for producing microalgae. For example, WO 00/61719 discloses that a high biomass productivity is a problem of optimum light distribution per unit volume. The known bioreactor has a reactor compartment made of translucent material, the enclosing end of which of the reactor chamber cross section is designed, for example, in a meander shape or sinusoidally to increase the surface area. Also, this publication discloses constructing the reactor chamber as glass tube into the interior of which project glass extensions.

It is a disadvantage that such a design of the enclosing ends of the reactor chamber is very complex and cost intensive.

Furthermore, DE 197 47 994 C1 discloses a bioreactor having U-shaped reactor elements. The U-shaped reactor elements consist of vertical transparent tubes which, at their lower ends, are connected to one another via a U-shaped leg. A tube of a reactor element acts as gas-introduction tube. For this, gas-introduction nozzles are provided as injectors for introducing carrier gases which simultaneously act for the transport of the culture medium in what is termed the airlift system. In the vertical direction, at the top end of the reactor elements, a reactor vessel is attached which forms a biomass collection chamber. The culture medium is heated or cooled via the reactor vessel which also simultaneously acts as expansion vessel and which has an exhaust gas apparatus.

It is a disadvantage of the known bioreactor that, owing to the arrangement of the U-shaped reactor elements, complete emptying of the bioreactor is relatively complex, since each of the reactor elements must be emptied separately. Also, it has been found that a spatial separation of heating or cooling device and exhaust gas apparatus, which would be advantageous for the closed-loop and open-loop control of the culture process, is only possible with difficulty in the known embodiment.

It is therefore an object of the present invention to improve the known apparatus in such a manner that its handling is simplified and that the closed-loop and open-loop control of the culture process can be improved.

SUMMARY OF THE INVENTION

This object is achieved in connection with a bioreactor for culturing microorganisms which has a reactor vessel in which the gas-introduction tubes are connected by their respective lower end, in the vertical direction, to the reactor vessel, and by their opposite upper end to an upper end of an upright vessel which is likewise connected by its lower end to the reactor vessel, and that at the upper end of the upright vessel an expansion vessel is disposed.

By means of the separation of reactor vessel and expansion vessel, heating or cooling device and exhaust air apparatus are spatially separated from one another, which simplifies the control, and in particular the cooling, of the gas to be discharged. By means of the arrangement of the reactor vessel at the lowest point, reliable complete emptying of the bioreactor can be achieved by a single outlet valve. U-tubes can be dispensed with completely. By means of the arrangement of the equalizing vessel of the upper end of the upright vessel, not only the gas-introduction tubes, but also the upright vessel, are bound into the equalization. The flow reversal is performed at the upper point which simplifies gas exchange or oxygen outlet.

According to a preferred embodiment of the invention, the gas-introduction tubes are constructed so as to be transparent at least in part, so that the bioreactor is also suitable for the culture of phototropic microorganisms.

According to a further preferred embodiment of the invention, the upright vessel is constructed as a standpipe having a circular cross section. The reactor vessel is, transverse to the vertical, likewise constructed with a circular shape, the standpipe being arranged centrally to the reactor vessel. The gas-introduction tubes are disposed in a circle shape around the standpipe. This achieves an apparatus which is compact and capable of scaleup. However, in principle, it is also possible to dispose the upright vessel and at least a part of the gas-introduction tubes in at least one vertical plane. In this case, the upright vessel, transverse to the vertical, can also have a cross section which is rectangular or shaped otherwise. By means of such a series arrangement, the system can be extended as desired.

According to a still further preferred embodiment of the invention, the upright vessel has an open cross-sectional area which approximately corresponds to the total of all open cross-sectional areas of the gas-introduction tubes. As a result, fluctuations in volumetric flow rate can be avoided, so that low pressure resistances occur. At the same time, it has been found that, to produce the flow velocity, significantly less gas is required than in known bioreactors which operate according to the airlift principle. As a result of the circulation in the cultivation vessels, unexpected dynamics form, which contribute to increasing the flow velocity.

According to another further preferred embodiment of the invention, the gas-introduction tubes are connected via tube bends to the expansion vessel. This is firstly, simpler in terms of assembly, and secondly the flow reversal is advantageously shifted to the expansion vessel. The expansion vessel has a lid on which are disposed a media feed device and an exhaust gas apparatus having exhaust-gas cooler and exhaust-gas sensor.

The gas-introduction tubes, the tube bends, the expansion vessel and the upright vessel are, according to a preferred embodiment, constructed of glass, for example borosilicate glass.

According to a further embodiment of the invention, the reactor vessel is constructed as a heat exchanger. The reactor vessel has in this case a reactor lower part having an outwardly dished base. In addition, the reactor lower part has an intermediate base which is dished into the biomass chamber and which, together with the outwardly dished base, forms a heating or cooling chamber. The reactor lower part is covered by an attachment lid having attachment flanges for the gas-introduction tubes, having an attachment flange for the sensors (pH, T, $pO_2$, optical density OD) and having an attachment flange for the upright vessel. Between attachment lid and intermediate base, the reactor lower part thus has a biomass chamber which advantageously has a smaller volume compared to the prior art and produces a turbulent flow with good mixing. The heating or cooling chamber can be heated or cooled via a heating or cooling device by feeding a heating or cooling medium, heat being exchanged between the heating or cooling chamber and the culture medium in the biomass chamber. The heating or cooling device advantageously consists of a closed hot water pressure system having a circulation pump and a heat exchanger for cooling water. The temperature of the culture medium can be used as control parameter. The reactor vessel and heat exchanger can additionally be provided with connections for an external heating or cooling circuit. By means of the chosen heat exchanger, firstly in a growth phase, a constant temperature can be maintained, and secondly, for initiating a stress phase for producing material of value, an elevated temperature can be achieved without problem and rapidly. Cooling is also possible in this manner without problems.

According to a still further preferred embodiment of the invention, a plurality of light sources of an illumination device is arranged adjacently to the gas-introduction tubes and the upright vessel. Depending on the size of the upright vessel, it is also possible that this has a vertical hollow chamber in which at least one light source is arranged. The vertical hollow chamber can be formed simply by a tube arranged in the upright vessel. The light sources are preferably constructed as fluorescent tubes which are arranged in parallel to the gas-introduction tubes and to the upright vessel. The illumination device or the light sources can, according to a further preferred embodiment, be dimmed. As a result, in particular in combination with an optical density measurement, closed-loop light control can be performed as a function of the concentration of the culture medium. By using a separate measurement light source, reproducible optical densities can be measured. For monitoring and open-loop control of the culture process, a digital measurement and control system is provided. In combination with appropriate measurement probes, such as temperature sensor, pH electrode, $pCO_2$ electrode and concentration monitor (measurement light source having absorption or density sensor), temperature, pH, $pCO_2$ value and optical density can be measured, subjected to closed-loop or open-loop control, and displayed.

BRIEF DESCRIPTION OF THE DRAWINGS

Further details of the invention are given by the extensive description and accompanying drawings hereinafter, in which preferred embodiments of the invention are illustrated by way of example.

DETAILED DESCRIPTION OF THE PREFERRED EMBODIMENTS

Figure 1:
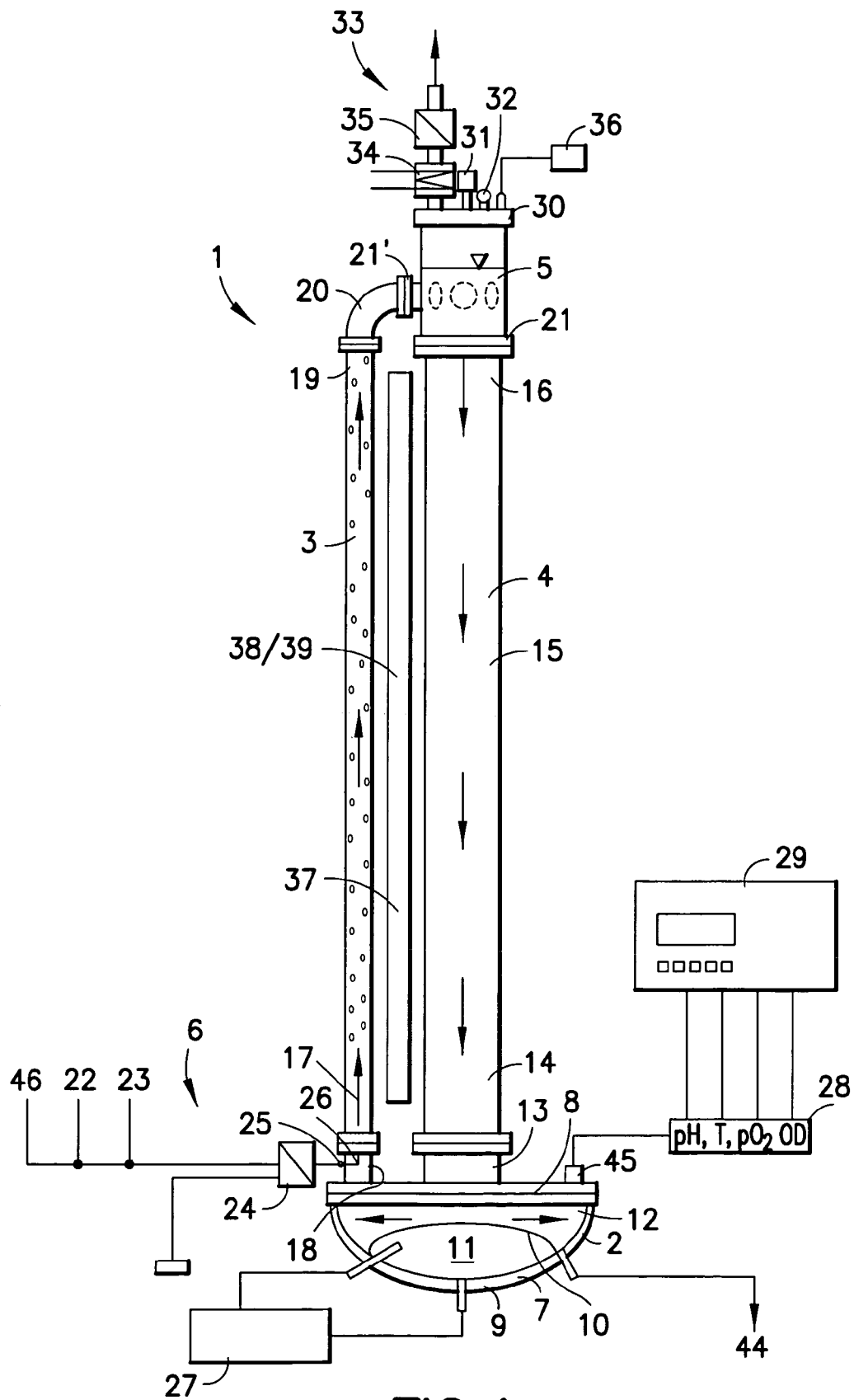
FIG. 1: shows a diagrammatic side view in section of a bioreactor.

A bioreactor 1 for the culture of phototropic microorganisms essentially consists of a reactor vessel 2, gas-introduction tubes 3, an upright vessel 4, an expansion vessel 5 and a gas-introduction system 6.

The reactor vessel 2 is constructed as a heat exchanger and consists of a reactor lower part 7 which is covered gas-tightly at the top, in the vertical direction, by an attachment lid 8. The reactor lower part 7 has an outward-dished base 9 and an inner-dished intermediate base 10. A heating or cooling chamber 11 is enclosed by the intermediate base and the base 9. The chamber enclosed by the base 9, intermediate base 10 and attachment lid 8 forms a biomass chamber 12. The reactor vessel 2 is designed as a jacketed stainless steel vessel and serves for heat transfer, measurement determination, and media removal (harvest material, wastewater) and sampling.

A harvest and base outlet valve 44 is built into the lowest part of the reactor vessel 2. It can be used for sample removal and product harvest after the end of the culture process, as outlet valve after cleaning the reactor vessel 2, but also for removing samples from the running process. The harvest and base outlet valve 44 can be sterilized in-situ. For this, it has a fixed-tube connection to the clean steam supply of the base apparatus. The first sterilization can be performed during the reactor sterilization, then the valve can also be sterilized after each sample removal.

Figure 2:
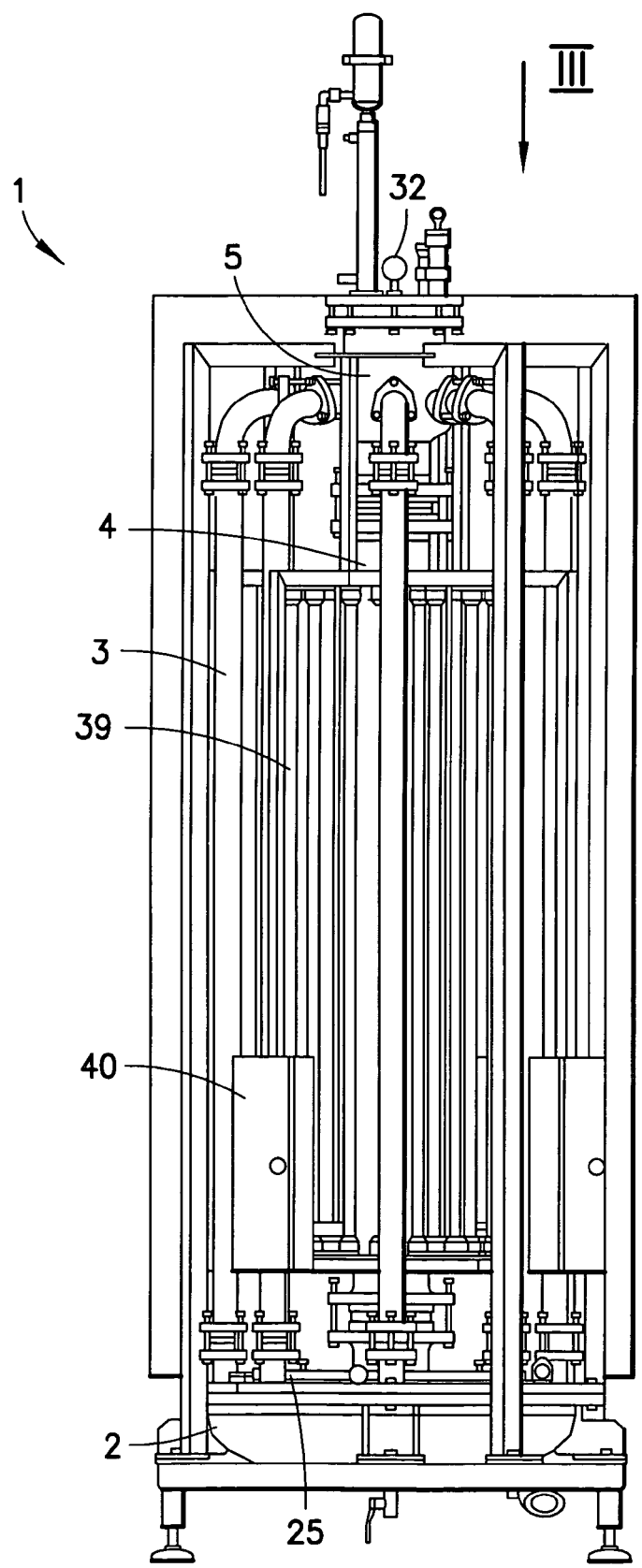
FIG. 2: shows a side view of a bioreactor.
Figure 3:
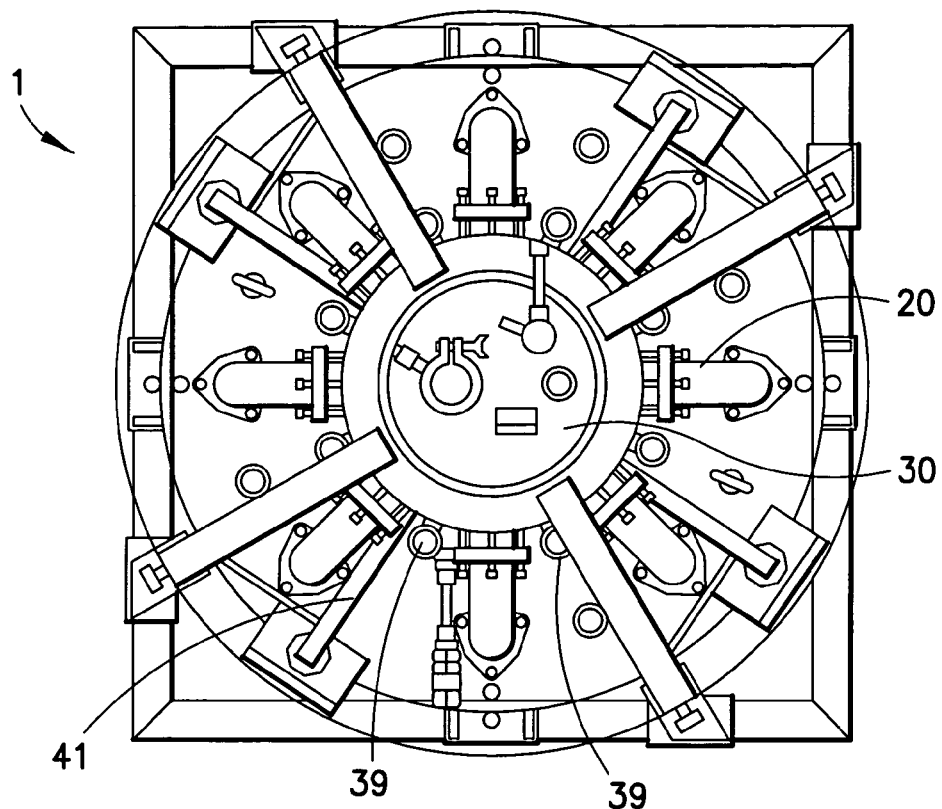
FIG. 3: shows a top plan view of the bioreactor of FIG. 2 from direction III in FIG. 2, and FIG. 4: shows a plan view of the illumination device of FIG. 2 in enlargement.
Figure 4:
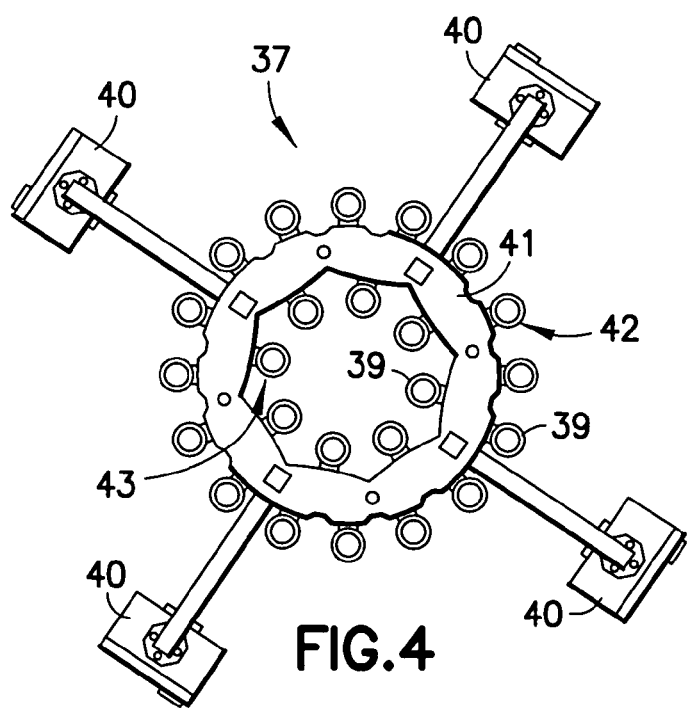

The upright vessel 4 which is constructed as standpipe 15 having a circular cross section is attached at a central attachment flange 13 of the attachment lid 8 by its lower end 14. The upright vessel 4 or the standpipe 15 has, at its upper end 16, the expansion vessel 5. The eight gas-introduction tubes 3 in the exemplary embodiment of FIG. 2 are distributed in a circle shape around the standpipe 15. The gas-introduction tubes 3 are joined by their lower ends 17 to connection flanges 18 of the attachment lid 8. At their upper ends 19, the gas-introduction tubes 3 are joined via tube bends 20 to flanges 21' of the expansion vessel 5. The expansion vessel 5 is joined via a flange 21 to the upright vessel.

The expansion vessel 5 serves for charging the entire system, for oxygen outlet and for liquid compensation in the event of temperature variations.

On the lid 30 of the expansion vessel 5, there are the following connections or elements:
safety valve 31,
pressure manometer 32,
exhaust gas apparatus 33 with exhaust gas cooler 34 and exhaust gas filter 35,
feed apparatus ($H_2O$, inoculum, nutrient solution ... ) 36,
two inoculation ports (Ø=25 mm, 50 mm) (not shown).

The expansion vessel 5 is dimensioned as a function of the plant size and is in the example approximately 14:1.

The gas-introduction system 6 has an air feed 22 and a $CO_2$ feed 23 via which the air or $CO_2$ are introduced into the culture medium via flow meters which are not shown, a feeder filter 24 and a gas-introduction ring 25 in the lower region of the gas-introduction tubes 3 or their attachment flanges 18 and via injectors 26. The gas-introduction ring 25 consists of a ring line having 8 lines to the gas-introduction tubes 3 and a feed line to the feed air filter or steam generator. The lines to the gas-introduction tube are in each case equipped with diaphragm valves for setting the flow rate (air, $CO_2$, steam).

The air/$CO_2$ ratio is mixed via a T-piece as a function of the culture conditions. Depending on requirements, the air or $CO_2$ are each fed via a float-type flow meter (air: 0 ... 30 l/min, $CO_2$: 0.15 ... 1.5 l/min). The $CO_2$ is fed customarily as control parameter as a function of pH, but can also optionally be metered as a constant volumetric flow rate. The $CO_2$ is metered via a $CO_2$ gas cylinder equipped with pressure reduced (max. 3 bar). The air and $CO_2$ are fed by the injector principle via the injectors 26 and produce, in the reactor vessel 2, a pressure deficit, which in turn makes possible circulation of the culture medium (suspension) in the upright vessel 4. The air and $CO_2$ throughput decisively determines the flow rate in the gas-introduction tubes 3, or in the upright vessel 4, and is set as a function of the gravity sensitivity of the culture medium or of the cultured microalga.

The culture medium is taken off from the reactor vessel 2 from the top via the gas-introduction tubes 3 and fed to the expansion vessel 5. The culture medium stream is thereafter fed back to the reactor vessel 2 via the central standpipe 15.

For the heating or cooling of the system, the heating or cooling chamber 11 is connected to a heating or cooling device 27.

The measurements (pH, T, OD, $pO_2$) are determined via sensors 28 which are disposed in the connection cover 8 through attachment flange 45 of the reactor vessel 2. The sensors 28 are connected to a digital measurement and control system 29.

The digital measurement and control system 29 is constructed in a waterspray-proof switch cabinet. It is based on a single board microcomputer system. It is operated via an integrated operation terminal with LCD display and film keyboard. The digital measurement and control system 29 has, inter alia, the following functions:
- temperature (measurement/control)
- pH (measurement/control),
- $pO_2$ (measurement),
- optical density (measurement) and
- air throughput (measurement/control).

A dimmable illumination device 37 consists, in the exemplary embodiment, of twenty-four light sources 38 which are constructed as fluorescent tubes 39, and also of four switch cabinets 40 and is accommodated in an illumination frame 41. In an outer illumination ring 42, sixteen fluorescent tubes 39 assigned to the gas-introduction tubes 3 are disposed, and in an inner illumination ring 43, eight fluorescent tubes 39 assigned to the standpipe 4 are disposed. Each switch cabinet 40 contains three electronic ballasts, which are not shown further for driving a group of six fluorescent lamps and a fan for cooling the ballasts. A switch cabinet serves as interface to the upstream control cabinet which is not further shown. Power supply and control signal for dimming are conducted to this switch cabinet via two separate lines from the control cabinet.

The illumination device can be used in manual or automatic operation. Manual operation can set, using a potentiometer, the desired light intensity (likewise at the front side of the control cabinet). In automatic operation, the light supply is controlled via the optical density (OD).

The culture medium flows into the gas-introduction tubes 3 at their lower end 17, circulates through the laterally offset vertical tubes up to the expansion vessel 5 and is returned to the reactor vessel 2 via the standpipe 15. The gas-introduction tubes 3 and the standpipe 15 are illuminated by the illumination device 37. The entire reactor system is sealed gas-tightly. By this means, the oxygen which is generated by the phototrophic growth of the microalgae cannot escape by the natural gas change. The extension vessel 5 collects the suspension or the culture medium and ensures an oxygen outlet, which is removed outward with the airstream via the exhaust gas cooler 34 and the exhaust gas filter 35. In the expansion vessel 5, the direction of flow is reversed.

The pH is under closed-loop control using a specific $CO_2$ feed via the injectors 26. At the same time, the $CO_2$ feed ensures the carbon fertilization of the microalgae.

The entire interior of the bioreactor 1 can be charged with superheated steam using a steam generator for sterilization. Superheated steam can be fed via a steam feed 46.

It will be understood by those skilled in the art that many modifications and variations of the present invention may be made without departing from the spirit and the scope thereof.

What is claimed is:

1. A bioreactor (1) for culturing microorganisms comprising a reactor vessel (2) which is constructed as a heat exchanger, a plurality of gas-introduction tubes (3) and a gas-introduction system (6) for introducing gas into a culture medium in the gas-introduction tubes (3) via injectors (26), wherein the gas-introduction tubes (3) are connected by their respective lower end (17), in the vertical direction, to the reactor vessel (2) and by their opposite upper end (19) to an upper end (16) of an upright vessel (4) which is likewise connected by its lower end (14) to the reactor vessel (2), and at the upper end (14) of the upright vessel (4) an expansion vessel (5) is arranged, said reactor vessel (2) having a reactor lower part (7) having a biomass chamber (12), and the reactor lower part (7) is covered by an attachment lid (8) which has attachment flanges (18) for the gas-introduction tubes (3), attachment flanges (45) for sensors (28) and an attachment flange (13) for the upright vessel (4).

2. The bioreactor as claimed in claim 1, wherein the gas-introduction tubes (3) are constructed so as to be at least in part transparent for the culture phototrophic microorganisms.

3. The bioreactor as claimed in claim 1, wherein the upright vessel (4) is constructed as a standpipe (15) having a circular cross section.

4. The bioreactor as claimed in claim 3, wherein the upright vessel (4) has an open cross-sectional area which approximately corresponds to the total of all open cross-sectional areas of the gas-introduction tubes (3).

5. The bioreactor as claimed in claim 4, wherein the expansion vessel (5) has a lid (30) on which are disposed a feed device (36) and an exhaust gas apparatus (33) having exhaust-gas cooler (34) and exhaust-gas filter (35).

6. The bioreactor as claimed in claim 1, wherein the gas-introduction tubes (3) are connected via the expansion vessel (5) to the upright vessel (4).

7. The bioreactor as claimed in claim 6, wherein the gas-introduction tubes are connected via tube bends (20) to the upright vessel (4).

8. The bioreactor as claimed in claim 7, wherein the gas-introduction tubes (3), the tube bends (20), the expansion vessel (5) and the upright vessel (4) are constructed of glass.

9. The bioreactor as claimed in claim 1, wherein the reactor lower part (7) has an outwardly dished base (9).

10. The bioreactor as claimed in claim 9, wherein the reactor lower part (7) has, in the biomass chamber (12), an inwardly dished intermediate base (10) which, together with the outwardly dished base (9), forms a heating or cooling chamber (11).

11. The bioreactor as claimed in claim 10, wherein the heating or cooling chamber (11) can be heated or cooled via a heating or cooling device (27) by feeding a heating or cooling medium, and, via the heating or cooling chamber (11), heat can be exchanged between the culture medium in the biomass chamber (12) and the heating or cooling medium in the heating or cooling chamber (11).

12. The bioreactor as claimed in claim 11, wherein the heating or cooling device (27) consists of a closed hot water pressure system having a circulation pump and a heat exchanger for cooling water, and the temperature of the culture medium can be used as control parameter.

13. The bioreactor as claimed in claim 12, wherein a plurality of light sources (38) of an illumination device (37) are arranged adjacently to the gas-introduction tubes (3) and the upright vessel (4).

14. The bioreactor as claimed in claim 13, wherein the upright vessel (4) has at least one vertical hollow chamber in which at least one light source (38) is arranged.

15. The bioreactor as claimed in claim 14, wherein the vertical hollow chamber is formed by a tube arranged in the upright vessel (4).

16. The bioreactor as claimed in claim 14, wherein the light sources (38) are constructed as fluorescent tubes (39) which are arranged in parallel to the gas-introduction tubes (3) and to the upright vessel (4).

17. The bioreactor as claimed in claim 16, wherein the illumination device (37) can be dimmed.

18. The bioreactor as claimed in claim 16, wherein a digital measurement and control system (29) is provided for monitoring and open-loop control of the culture process.

19. The bioreactor as claimed in claim 18, wherein the digital measurement and control system (29) is suitable for the measurement and display of temperature, pH, $pO_2$ and optical density.

20. The bioreactor as claimed in claim 19, wherein the standpipe (4) is constructed centrally to the reactor vessel (2) which is constructed so as to be circular transversely to the vertical and the gas-introduction tubes (3) are arranged in a circle shape around the standpipe (4).

21. The bioreactor as claimed in claim 19, wherein the upright vessel (4) and at least a part of the gas-introduction tubes (3) are arranged in at least one vertical plane.

22. The bioreactor as claimed in claim 21, wherein the reactor vessel (2) transforms at least in part into a horizontal lower connection tube to which the lower ends of the gas-introduction tubes are flanged, and an upper connection tube is provided to which the upper ends (19) of the gas-introduction tubes (3) are connected to the upper end (16) of the upright vessel (4), or to the expansion vessel (5) arranged at the upper end (16) of the upright vessel (4).

* * * * *